US012654026B2

(12) United States Patent
Varghese et al.

(10) Patent No.: US 12,654,026 B2
(45) Date of Patent: Jun. 16, 2026

(54) ACNE-TREATMENT SYSTEM WITH PROCESSING UNIT

(71) Applicant: KONINKLIJKE PHILIPS N.V., Eindhoven (NL)

(72) Inventors: Babu Varghese, Eindhoven (NL); Yannyk Parulian Julian Bourquin, Eindhoven (NL); Jonathan Alambra Palero, Waalre (NL); Willem Verkruijsse, Veldhoven (NL); Elvira Johanna Maria Paulussen, Reppel-Bocholt (NL); Kiran Kumar Thumma, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

(21) Appl. No.: 18/712,318

(22) PCT Filed: Nov. 17, 2022

(86) PCT No.: PCT/EP2022/082175
§ 371 (c)(1),
(2) Date: May 22, 2024

(87) PCT Pub. No.: WO2023/094246
PCT Pub. Date: Jun. 1, 2023

(65) Prior Publication Data
US 2025/0010093 A1      Jan. 9, 2025

(30) Foreign Application Priority Data
Nov. 25, 2021      (EP) ..................................... 21210496

(51) Int. Cl.
*A61N 5/06*              (2006.01)

(52) U.S. Cl.
CPC .... *A61N 5/0616* (2013.01); *A61N 2005/0626* (2013.01); *A61N 2005/0644* (2013.01); *A61N 2005/0663* (2013.01)

(58) Field of Classification Search
CPC .......... A61N 5/0616; A61N 2005/0626; A61N 2005/0644; A61N 2005/0663;
(Continued)

(56) References Cited

U.S. PATENT DOCUMENTS 6,393,315 B1      5/2002  Aprahamian et al.
6,676,654 B1      1/2004  Balle-Petersen et al.
(Continued)

FOREIGN PATENT DOCUMENTS

CN        112873286      *  1/2021  .......... A61B 6/0077
CN        112873286 A      6/2021
(Continued)

OTHER PUBLICATIONS

Zhao et al. "Therapeutic effect of alternating red and blue light irradiation combined with collagen in patients with acne vulgaris and the risk factors of short-term recurrence" Am J Transl Res 2022;14(11):7870-7879 (Year: 2022).*
(Continued)

*Primary Examiner* — Nathan J Jenness

(57)              ABSTRACT

According to an aspect, there is provided an acne-treatment system comprising a processing unit (40) and an acne-treatment apparatus (46; 52) configured to treat an acne lesion on skin of a subject by means of first treatment light having wavelengths predominantly in a range from 600 to 700 nm and second treatment light having wavelengths predominantly in a range from 400 to 480 nm, the processing unit (40) being configured to: receive one or more measurement signals provided by one or more sensors (42) that are configured and arranged to measure one or more
(Continued)

parameters indicative of a degree of inflammation and/or a severity phase of the acne lesion, said one or more measurement signals representing an indicated degree of inflammation and/or an indicated severity phase of the acne lesion; determine a light-intensity ratio of intensity of the first treatment light to intensity of the second treatment light to be applied to the acne lesion based on the indicated degree of inflammation and/or the indicated severity phase of the acne lesion represented by the one or more measurement signals; and control one or more light sources (44) of the acne-treatment apparatus (46; 52) to generate the first treatment light and the second treatment light according to the determined light-intensity ratio for application to the acne lesion.

17 Claims, 5 Drawing Sheets

(58) Field of Classification Search
CPC ............ A61N 2005/0628; A61B 5/445; A61B 5/4836; B26B 11/008; G16H 20/40; G16H 50/20; G16H 50/30
See application file for complete search history.

(56) References Cited

U.S. PATENT DOCUMENTS

| | | |
|---|---|---|
| 8,313,518 B2 | 11/2012 | Ripper |
| 2002/0173833 A1 | 11/2002 | Korman et al. |
| 2004/0225339 A1 | 11/2004 | Yaroslavsky et al. |
| 2006/0030908 A1 | 2/2006 | Powell et al. |

| | | | | |
|---|---|---|---|---|
| 2008/0103560 A1* | 5/2008 | Powell | ................. | A61N 5/0616 607/94 |
| 2008/0119913 A1* | 5/2008 | Powell | ................. | A61N 5/0616 606/9 |
| 2009/0177253 A1 | 7/2009 | Darm et al. | | |
| 2010/0100160 A1* | 4/2010 | Edman | ................... | A61B 5/444 607/88 |
| 2016/0016001 A1 | 1/2016 | Loupis et al. | | |
| 2017/0246473 A1 | 8/2017 | Marinkovich et al. | | |
| 2017/0370992 A1* | 12/2017 | Heubach | .............. | G01R 31/327 |
| 2022/0055237 A1* | 2/2022 | Cordani | ................. | B26B 19/46 |

FOREIGN PATENT DOCUMENTS

| | | | | | |
|---|---|---|---|---|---|
| JP | 2010264276 A | | 11/2010 | | |
| JP | 6895603 B | | 6/2021 | | |
| KR | 20150008258 A | | 1/2015 | | |
| KR | 20190062180 A | | 6/2019 | | |
| WO | WO 2008052151 A2 | * | 5/2008 | ........... | A61N 5/0616 |
| WO | 2019093787 A2 | | 5/2019 | | |

OTHER PUBLICATIONS

Lee et al., "Blue and Red Light Combination LED Phototherapy for Acne Vulgaris in Patients with Skin Phototype IV", Lasers in Surgery and Medicine 39:180-188 (2007).
Papegeorgiou et al., "Phototherapy with blue (415 nm) and red (660 nm) light in the treatment of acne vulgaris British Journal of Dermatology", vol. 142 Issue 5, pp. 973-978, (2000).
Ammad et al,., "An assessment of the efficacy of blue light phototherapy in the treatment of acne vulgaris", Journal of Cosmetic Dermatology, vol. 7: 180-188. (2008).
International Search report and Written Opinion of PCT/EP2022/082175, dated Feb. 16, 2023.

* cited by examiner

ACNE-TREATMENT SYSTEM WITH PROCESSING UNIT

CROSS-REFERENCE TO PRIOR APPLICATIONS

This application is the U.S. National Phase application under 35 U.S.C. § 371 of International Application No. PCT/EP2022/082175, filed on Nov. 17, 2022, which claims the benefit of European Patent Application No. 21210496.2, filed on Nov. 25, 2021. This application is hereby incorporated by reference herein.

FIELD OF THE INVENTION

This disclosure relates to treatment of an acne lesion on skin of a subject, and in particular to an acne-treatment system comprising a processing unit and an acne-treatment apparatus that treats an acne lesion by means of light.

BACKGROUND OF THE INVENTION

A recent focus in the field of personal care devices, and in particular facial hair shaving devices, is the addition of functions to enable such a device to provide benefits or treatments to a user of the device in addition to the primary personal care function performed by the device, such as shaving, hair removal, skin massage, etc.

For example, an enhanced sensorial experience may be provided to the user of a personal care device via the use of an infra-red (IR) or Near IR (NIR) light module within the personal care device. The IR or Near IR light module may be powered to provide gentle warmth to the user and/or treat the skin of the user while the personal care device is in use performing the personal care function(s).

A further treatment that can be provided by a personal care device, particularly one that is used on the face, is the treatment of acne using light. Light therapy with blue and red light, which combines an antibacterial effect (due to optimum photoexcitation of *Propionibacterium acnes* bacteria) and an anti-inflammatory action (due to cytokine release from macrophages), is an effective means of treating acne vulgaris that has a mild to moderate severity, with no significant short-term adverse effects.

Acne lesions can be subdivided into different types of lesions; microcomedones, blackheads, whiteheads, papules, pustules, nodules, cysts, macules and scars. Inflammation is a reaction to infectious or sterile tissue damage and has the physiological purpose of restoring tissue. Inflammation plays a major role in containing and resolving infection or damage and may also occur under sterile conditions. Comedones are the biggest precursor to inflammatory acne lesions. Comedones do not always turn into inflammation or nodules. Comedone can transition to an inflammatory papule/pustule. This transition is usually called inflammation. The inflammation in acne varies throughout the acne lesion's lifecycle, from non-inflammatory microcomedones to closed and open comedones to inflammatory lesions (papules, pustules, nodules, and "cysts"), and eventually to post acne lesions (post-inflammatory erythema (PIE), post-inflammatory hyperpigmentation (PIH), normal skin or scarring).

Clinical types of acne include (1) non-inflammatory comedonal acne (comedones only; no inflammatory lesions or cysts); (2) mild inflammatory acne (inflammatory papules and comedones); (3) moderate inflammatory acne (inflammatory papules, pustules and comedones in overall greater number than mild disease); and (4) severe inflammatory nodulocystic acne (inflammatory papules, comedones and cysts with residual scarring).

FIG. 1 illustrates the inflammation process and clinical appearance for acne lesions over the course of time. The onset stage can last a few hours and includes inflammatory cell infiltration and occurrence of inflammation effects, such as swelling (oedema), redness, heat and/or pain. The resolution stage can last for several days and includes inflammatory cell clearance and reduction of swelling (oedema), redness, heat and/or pain. The healing stage can last for several weeks, and redness in the skin can be perceived due to formation of granulation tissue and remodelling of the skin.

SUMMARY OF THE INVENTION

It has been found that in the case of acne lesions, the optimal light treatment (in terms of the wavelengths of light used, their relative intensities, etc.) depends on the stage at which the lesion is at. For example, red light should have a relatively higher intensity than blue light when the lesion is at a high inflammation stage, and vice versa in a low inflammation stage. However, a particular subject or user with acne will typically have acne lesions at a variety of different stages, and therefore there will not be a single configuration for the light treatment that is optimal for all of their acne lesions.

WO 2008/052151 discloses a personal care device comprising a shaving device component and a phototherapy device component. The use of red and blue light is described, and a combination of different wavelengths of light may be applied simultaneously to treat different skin conditions at the same time. A user is able to control the wavelengths emitted and the intensity levels just by selecting a particular skin condition, with the control system causing the device to provide appropriate colours and intensity for that skin condition.

While WO 2008/052151 enables a user to select a skin condition and the control system uses predetermined colours and intensity for that skin condition, it is typically difficult for a user of a personal care device to correctly ascertain a type of skin condition that is to be treated. Moreover, WO 2008/052151 does not recognise that it may be beneficial to tune the characteristics of the emitted light to a particular stage of an acne lesion, and does not describe that variations in the inflammation state can be used as a discriminator for characterising the phases in the lifecycle of a pimple/acne lesion, in particular the maturity phase of an acne lesion when the inflammation is at its peak and also how it changes in response to a light treatment.

Treatment of a skin region with acne lesions without knowledge of the maturity phase/stage of the lesions may lead to over- or under-treatment, resulting in undesirable side effects and poor treatment efficacy. Furthermore, a user may have different acne lesions at different maturity stages, which may mean that the optimum light characteristics may be different for different parts of the body/face.

Therefore it is an objective of this disclosure to provide an acne-treatment system comprising a processing unit and an acne-treatment apparatus that can be used with, or as part of, a personal care device (including shaving systems) to provide an improved treatment of acne lesions that provides appropriate red and blue light intensities based on the current physiological stage of the acne lesion, and thereby improve the treatment efficacy and reduce side effects.

According to a first aspect of the invention, there is provided an acne-treatment system comprising a processing unit and an acne-treatment apparatus having one or more light sources configured and arranged to generate first treatment light having wavelengths predominantly in a range from 600 to 700 nm and second treatment light having wavelengths predominantly in a range from 400 to 480 nm for application to an acne lesion on skin of a subject during use of the acne treatment system. The processing unit is configured to: receive one or more measurement signals provided by one or more sensors that are configured and arranged to measure one or more parameters indicative of a degree of inflammation and/or a severity phase of the acne lesion, said one or more measurement signals representing an indicated degree of inflammation and/or an indicated severity phase of the acne lesion; determine a light-intensity ratio of intensity of the first treatment light to intensity of the second treatment light to be applied to the acne lesion based on the indicated degree of inflammation and/or the indicated severity phase of the acne lesion represented by the one or more measurement signals; and control the one or more light sources of the acne-treatment apparatus to generate the first treatment light and the second treatment light according to the determined light-intensity ratio for application to the acne lesion.

In an embodiment of an acne-treatment system according to the first aspect, the acne-treatment apparatus comprises the processing unit of the acne-treatment system.

In an embodiment of an acne-treatment system according to the first aspect, the acne-treatment system comprises a control apparatus comprising the processing unit of the acne-treatment system and a first communication unit. The acne-treatment apparatus of the acne-treatment system has a second communication unit configured to communicate with the first communication unit. During use, a control signal generated by the processing unit to control the one or more light sources of the acne-treatment apparatus is communicated from the control apparatus to the acne-treatment apparatus via the first and second communication units.

According to a second aspect of the invention, there is provided an electric shaving apparatus comprising an acne-treatment system according to the first aspect or any embodiment thereof, and further comprising a main body and a shaving unit coupled to the main body. The one or more light sources of the acne-treatment apparatus are arranged in the shaving unit to apply the first treatment light and the second treatment light to the skin of the subject during operation of the shaving unit with the shaving unit in contact with the skin of the subject.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF THE EMBODIMENTS

As noted above, it is an objective of this disclosure to provide an acne-treatment system comprising a processing unit and an acne-treatment apparatus to provide an improved treatment of acne lesions. The processing unit of the acne-treatment system provides the improvements by automatically determining a ratio of light intensities that is appropriate for the current physiological stage of the acne lesion, and thereby improve the treatment efficacy and reduce side effects provided by the light treatment. In some implementations, the acne-treatment system may be used with, or as part of, a personal care device (including shaving systems).

Figure 1:
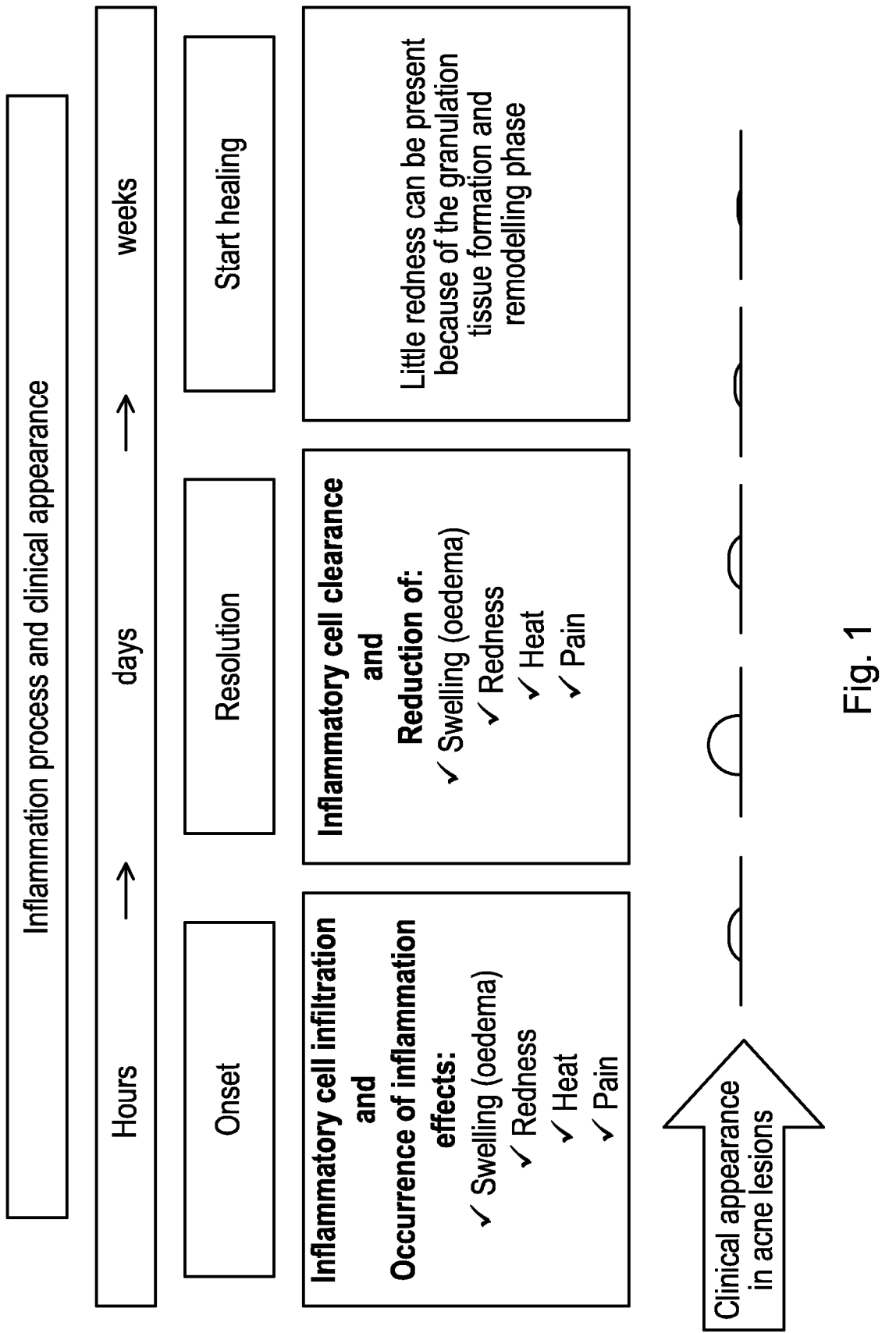
FIG. 1 illustrates the inflammation process and clinical appearance for acne lesions over the course of time.
Figure 2:
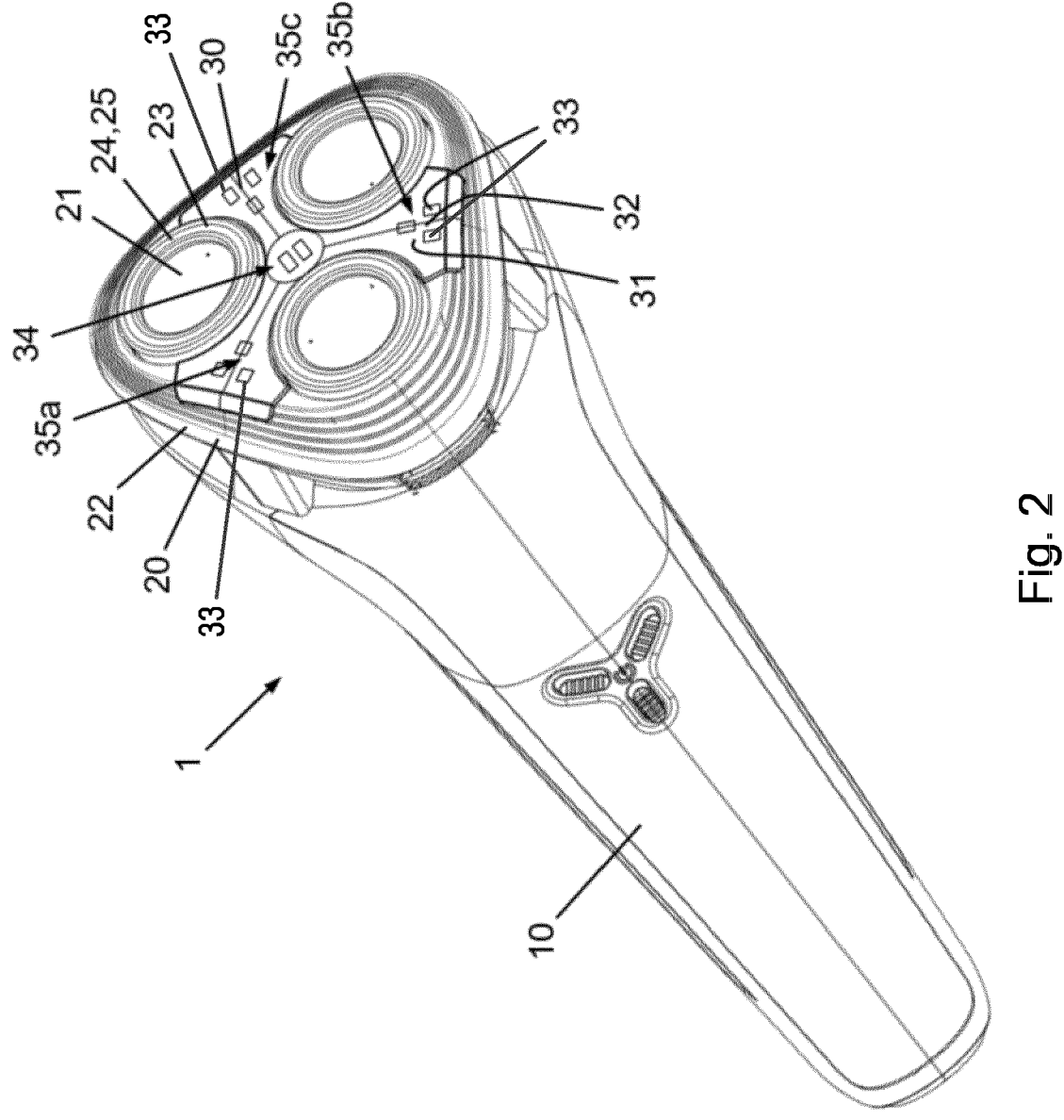
FIG. 2 is a simplified illustration of an electric shaver.

FIG. 2 is a simplified illustration of an electric shaving apparatus 1. The illustrated electric shaving apparatus 1 is also an acne-treatment apparatus as it comprises one or more light sources for performing a treatment operation on acne lesions, the processing unit according to the techniques described herein that controls the light source(s) can be part of the electric shaving apparatus 1, or separate from the electric shaving apparatus 1.

In the shown example, the electric shaving apparatus 1 is of the rotary type and comprises a main body 10 that is intended to be held by a user of the electric shaving apparatus 1, and a functional unit 20 that is intended to contact a portion of skin to perform a personal care function. In this example the functional unit 20 is a shaving unit, and the personal care operation is shaving/hair cutting/hair trimming. The main body 10 of the electric shaving apparatus 1 is also commonly referred to as handle, and the shaving unit 20 of the electric shaving apparatus 1 is also commonly referred to as a shaving head.

The shaving unit 20 includes a number of hair-cutting units 21, the number being three in the shown example. When the electric shaving apparatus 1 is applied to skin to perform a shaving action, the actual process of cutting off hairs protruding from the portion of skin takes place at the position of the hair-cutting units 21. For the purpose of supporting the hair-cutting units 21, the shaving unit 20 comprises a base member 22.

Each of the hair-cutting units 21 comprises a combination of an external cutting member 23 that is of a generally cup-shaped design and an internal cutting member (not shown) that is equipped with at least one hair-cutting element and that is at least partially accommodated in the interior of the external cutting member 23. The external cutting member 23 has hair-entry openings 24 in an annular cutting track surface 25. During a shaving action, hairs extending through the hair-entry openings 24 and protruding to the interior of the external cutting member 23 are cut off as soon as they are encountered by a hair-cutting element of the internal cutting member. A shaving action is performed when the internal cutting member is activated to rotate and a portion of skin is actually contacted by the external cutting member 23 at the position of the cutting track surface 25. Activation of the internal cutting member may take place in a known manner by means of a drive mechanism of the electric shaving apparatus 1. This drive mechanism (e.g. a motor), is typically located in the main body 10, and the rotational movement of the motor is transferred to the internal cutting members of the hair-cutting units 21 in the shaving unit 20. When the combination of the external cutting member 23 and the internal cutting member is moved over the portion of skin while the internal cutting member is driven to rotate, it is achieved that hairs protruding from the portion of skin are caught in the hair-entry openings 24 of the external cutting member 23 and are cut off in that position.

In the electric shaving apparatus 1 shown in FIG. 2, the shaving unit 20 comprises a light unit 30 that is configured to emit light on to the skin to provide a treatment effect on acne lesions. The light unit 30 can comprise a skin-contacting member 31 having a skin-contacting surface 32 that is arranged adjacent to the hair-cutting units 21 to contact the skin during a shaving action. Further, the light unit 30 comprises a plurality of light sources 33, which will hereinafter be simply referred to as light sources 33 for the sake of clarity, and which may be LEDs or laser diodes, for example. Each light source may be configured to emit light at specific wavelengths, or may be controllable to emit light at varying wavelengths. For example one or more light sources can be provided that emit light that is predominately red (e.g. with wavelengths predominately in the range from 600 to 700 nm), and one or more other light sources can be provided that emit light that is predominately blue/violet (e.g. with wavelengths predominately in the range from 400 to 480 nm). Alternatively, each light source can be controllable to alternately emit light that is predominately red and light that is predominately blue/violet. The light sources 33 may be integrated in the skin-contacting member 31. The skin-contacting member 31 may comprise material that is transparent to the wavelengths of light emitted by the light source(s) 33, and the light sources 33 may be embedded in the material. When the light unit 30 is activated during a shaving action, it is achieved that the skin is subjected to more actions besides the shaving action, in particular actions in which acne lesions are treated, which may lead to improvement of the condition/appearance of the acne lesions.

In the shown example, the skin-contacting member 31 is provided in the form of a bracket that is arranged to extend between and partially support the three hair-cutting units 21. According to an advantageous option, the skin-contacting member 31 including the light sources 33 is removably or hingably arranged in the shaving unit 20. In order to have a practical distribution of the emitted light, the light sources 33 can be arranged to emit the light via a central section of the skin-contacting surface 32 arranged between the hair-cutting units 21 and via peripheral sections 35a, 35b, 35c of the skin-contacting surface 32 arranged between each of the three different pairs of adjacent hair-cutting units 21 in the equilateral triangular configuration.

The shaving unit 20 shown in FIG. 2 also comprises one or more sensors 34 that are for measuring one or more parameters of acne lesions on the skin. The one or more sensors 34 output respective measurement signals that are representative of the measured parameter(s). The one or more parameters are indicative of the degree of inflammation and/or severity phase of an acne lesion on the skin. In alternative implementations, the one or more sensors 34 can be provided separately from the electric shaving apparatus 1.

Figure 3:
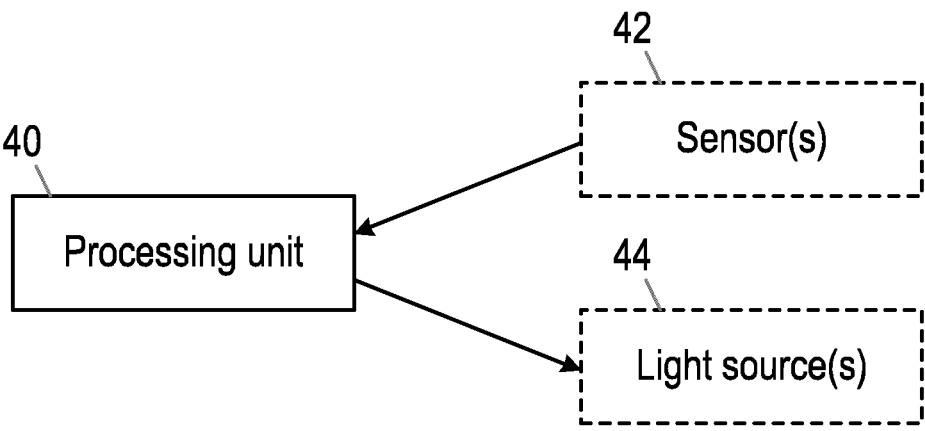
FIG. 3 illustrates a processing unit according to the techniques described herein along with one or more sensors and one or more light sources.

FIG. 3 illustrates a processing unit 40 according to the techniques described herein along with one or more sensors 42 and one or more light sources 44. The one or more light sources 44 are part of an acne-treatment apparatus.

The processing unit 40 performs the techniques described herein of determining a ratio of light intensities that is appropriate for the current physiological stage of an acne lesion and controlling the operation of the one or more light sources 44 to generate the appropriate treatment light. The processing unit 40 determines the ratio based on one or more measurement signals received from the one or more sensors 42.

The processing unit 40 can be implemented in numerous ways, with software and/or hardware, to perform the various functions described herein. The processing unit 40 may comprise one or more microprocessors or digital signal processors (DSPs) that may be programmed using software or computer program code to perform the required functions and/or to control components of the processing unit 40 to effect the required functions. The processing unit 40 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), field-programmable gate arrays (FPGAs), hardware for implementing a neural network and/or so-called artificial intelligence (AI) hardware accelerators (i.e. a processor(s) or other hardware specifically designed for AI applications that can be used alongside a main processor).

Although not shown in FIG. 3, the processing unit 40 can be connected to a memory unit that can store data, information and/or signals for use by the processing unit 40 in executing or performing the techniques described herein. In some implementations the memory unit stores computer-readable code that can be executed by the processing unit 40 so that the processing unit 40 performs one or more functions, including the techniques described herein. The memory unit can comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM) and electrically erasable PROM (EEPROM), and the memory unit can be implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

The one or more sensors 42 are for measuring one or more parameters of acne lesions on the skin of a subject. In particular, the one or more parameters are indicative of the degree of inflammation and/or severity phase of an acne lesion on the skin. The sensor(s) 42 output respective measurement signals that are representative or indicative of the measured parameter(s). The one or more parameters indicative of the degree of inflammation of the acne lesion can be any of: the redness of the acne lesion, the blood oxygenation in the acne lesion, the haemoglobin and/or oxyhaemoglobin level in the acne lesion, the temperature of the acne lesion, and the blood perfusion in the acne lesion. The one or more sensors 42 can include any one or more of an imaging sensor (e.g. a digital camera), a laser speckle contrast analysis (LASCA) imaging sensor, a laser Doppler perfusion monitor, a photoplethysmogram (PPG) imaging sensor, a PPG sensor, a multispectral/hyperspectral imaging sensor, a skin reflectance sensor and a temperature sensor. A digital hyperspectral imaging sensor can image underlying tissue and/or blood vessels, for example tissue oxygen saturation (known as StO2). A LASCA imaging sensor or a laser Doppler perfusion monitor can be used to measure blood perfusion. A PPG sensor can be used to measure oxygenation of the blood. A temperature sensor can measure the temperature of the skin, which is related to the local inflammation level of the skin.

Depending on the type of sensor 42, the measurement signal output by the sensor 42 may relate to a particular part of the skin of the subject, and thus one particular acne lesion, or the measurement signal may represent or be indicative of multiple measurements of the parameter at different locations on the skin. For example an image of the skin may include information on multiple acne lesions. In the former case (i.e. where the measurement signal relates to one, or just a few acne lesions), multiple sensors 42 (of the same type) may be provided in order to obtain measurements of parameters relating to different parts of the skin. In some embodiments, to improve the evaluation of the inflammation stage and/or severity of the acne lesions, multiple types of sensors 42 can be provided that measure respective parameters.

The one or more light sources 44 may be LEDs or diode lasers, for example. Each light source 44 may be configured to emit light at specific wavelengths, or may be controllable to emit light at varying wavelengths. For example one or more light sources 44 can be provided that generate and emit light that is predominately red (e.g. with wavelengths predominately in the range from 600 to 700 nm), and one or more other light sources 44 can be provided that generate and emit light that is predominately blue/violet (e.g. with wavelengths predominately in the range from 400 to 480 nm). Alternatively, each light source 44 can be controllable to alternately generate and emit light that is predominately red and light that is predominately blue/violet. Further to the above, and in connection with each wavelength range as described herein with reference to the invention and the embodiments thereof, the term "predominantly" implies that at least 80%, preferably at least 90%, and more preferably at least 95% of the optical power of each of the first treatment light and the second treatment light is provided by wavelength components within the respectively defined wavelength range. In the case of an LED light source, for example, the LED may have a bandwidth of 20-40 nm, and with a suitable peak wavelength in one of the ranges specified above, all of the emitted light will be within the wavelength ranges.

As noted above, the light source(s) 44 are part of an acne-treatment apparatus. The processing unit 40 may be part of the acne-treatment apparatus, or part of a separate control apparatus of an acne-treatment system that comprises the acne-treatment apparatus. Likewise, the sensor(s) 42 may be part of the acne-treatment apparatus, or part of a separate apparatus of an acne-treatment system (including part of a separate apparatus to the control apparatus in which the processing unit is implemented). In some embodiments, the acne-treatment apparatus is part of, or integrated with, a personal care device, such as an electric shaving apparatus. In this way the personal care device is able to provide the acne treatment operation in addition to the usual personal care functions of the personal care device.

Figure 4:
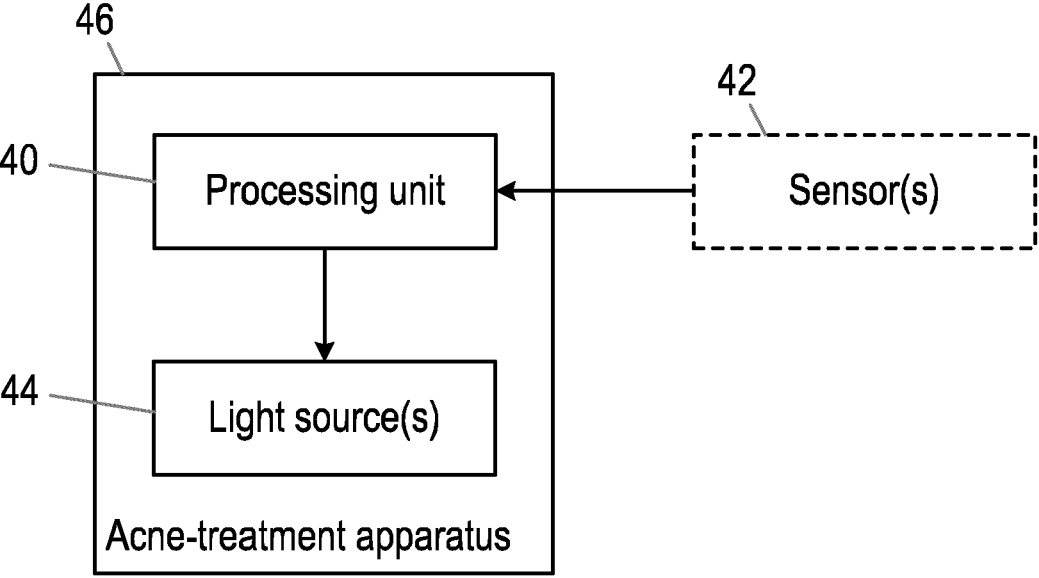
FIG. 4 is a block diagram illustrating the processing unit of FIG. 3 as part of an acne-treatment apparatus.
Figure 5:
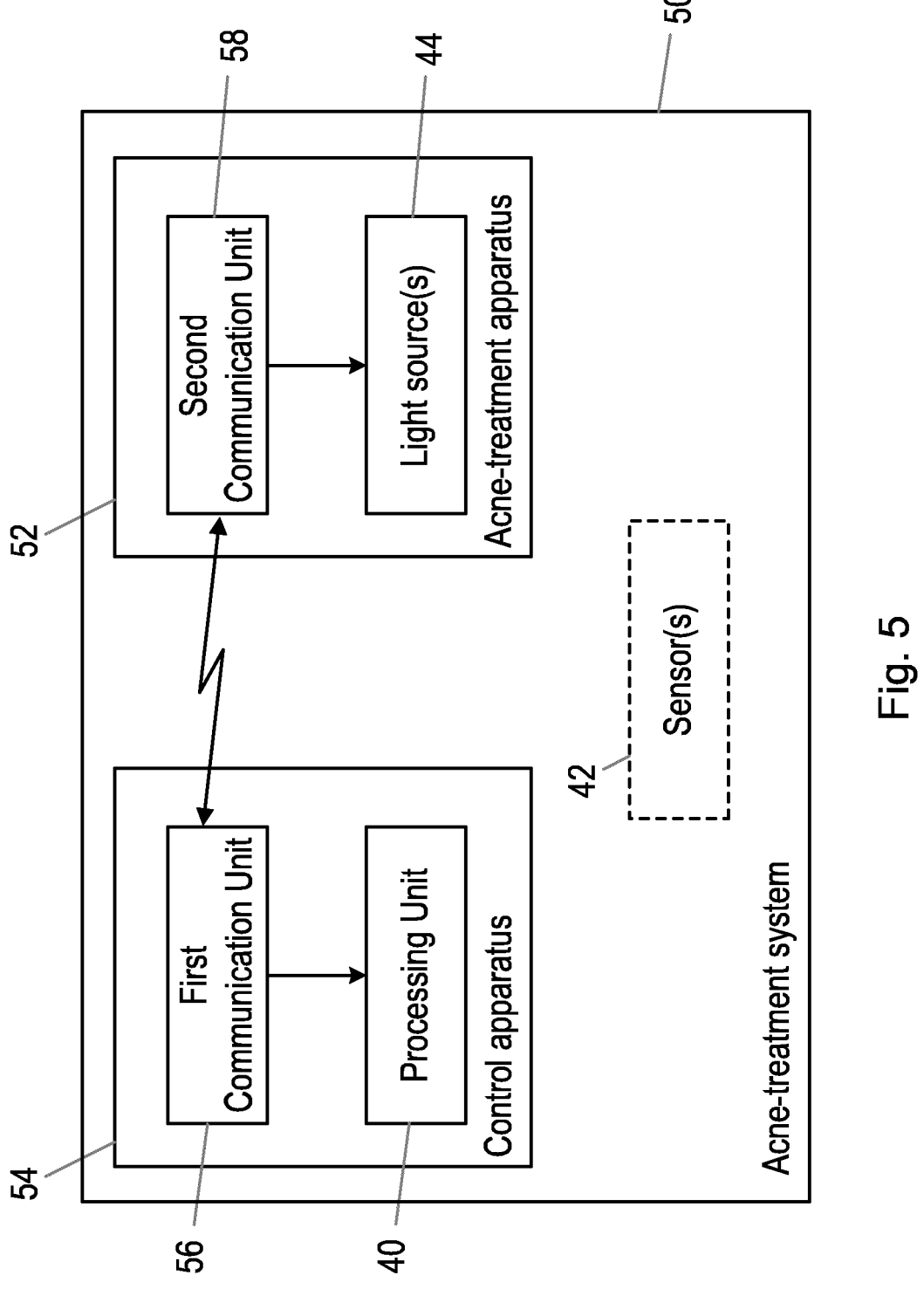
FIG. 5 is a block diagram illustrating the processing unit of FIG. 3 as part of a control apparatus in an acne-treatment system.

FIGS. 4 and 5 are block diagrams illustrating two exemplary implementations of processing unit 40 and an acne-treatment apparatus. In particular, FIG. 4 shows the processing unit 40 as part of an acne-treatment apparatus 46. The acne-treatment apparatus 46 comprises the light source(s) 44. The acne-treatment apparatus 46 can be a dedicated acne-treatment apparatus, i.e. acne treatment is the primary or sole function of the apparatus 46, or the acne-treatment apparatus 46 can be part of a personal care device that provides another personal care operation in addition to acne treatment. Such a personal care operation can be shaving or hair cutting/trimming. The sensor(s) 42 can be part of the acne-treatment apparatus 46, or in a separate unit or apparatus. In the latter case, the processing unit 40 can be configured to receive measurement signal(s) from the sensor(s) 42, for example via one or more communication units (not shown in FIG. 4).

FIG. 5 shows the processing unit 40 as part of an acne-treatment system 50. The acne-treatment system 50 comprises an acne-treatment apparatus 52 that comprises the light source(s) 44, and a control apparatus 54 that comprises the processing unit 40. The control apparatus 54 comprises a first communication unit 56 and the acne-treatment apparatus 52 comprises a second communication unit 58. The communication units 56, 58 enable the communication of data or signals between the control apparatus 54 and the acne-treatment apparatus 52. For example, the communication units 56, 58 can enable the communication of a control signal from the processing unit 40 to the light source(s) 44 so that the processing unit 40 can control the operation of the light source(s) 44. The acne-treatment apparatus 52 can be a dedicated acne-treatment apparatus, i.e. acne treatment is the primary or sole function of the apparatus 52, or the acne-treatment apparatus 52 or acne-treatment system 50 can be part of a personal care device or personal care system that provides another personal care operation in addition to acne treatment. Such a personal care operation can be shaving or hair cutting/trimming. The sensor(s) 42 can be part of the acne-treatment apparatus 52, part of the control apparatus 54, or part of a separate unit or apparatus in the acne-treatment system 50. Where the sensor(s) 42 are separate from the control apparatus 54, the first communication unit 56 can enable the processing unit 40 to receive the measurement signal(s) from the sensor(s) 42.

The control apparatus 54 can be any type of electronic device or computing device. For example, the control apparatus 54 can be, or be part of, a smartphone, a tablet, a smart watch, a smart mirror, a laptop, a computer or a server, for example a server in a data centre (also referred to as being 'in the cloud').

As noted, the first communication unit 56 and the second communication unit 58 enable a data connection and/or data exchange between the control apparatus 54 and the acne-treatment apparatus 52, and optionally also the sensor(s) 42, depending on the implementation. The connection may be direct or indirect (e.g. via the Internet), and thus the communication units 56, 58 can enable a connection between the control apparatus 54 and the acne-treatment apparatus 52 via a network (such as the Internet), or directly between the control apparatus 54 and the acne-treatment apparatus 52, via any desirable wired or wireless communication protocol. For example, the communication units 56, 58 can operate using WiFi, Bluetooth, Zigbee, or any cellular communication protocol. In the case of a wireless connection, the communication units 56, 58 (and thus control apparatus 54 and acne-treatment apparatus 52) may include one or more suitable antennas for transmitting/receiving over a transmission medium (e.g. the air). Alternatively, in the case of a wireless connection, the communication units 56, 58 may include means (e.g. a connector or plug) to enable the communication units 56, 58 to be connected to one or more suitable antennas external to the control apparatus 54 and acne-treatment apparatus 52 for transmitting/receiving over a transmission medium (e.g. the air). The first communication unit 56 is connected to the processing unit 40 to enable information or data received by the first communication unit 56 to be provided to the processing unit 40, and/or information or data from the processing unit 40 to be transmitted by the first communication unit 56.

Although not shown in FIG. 3, 4 or 5, a user interface may be provided that includes one or more components that enables a user of acne-treatment apparatus 46, 52 and/or control apparatus 54 (e.g. the subject) to input information, data and/or commands into the acne-treatment apparatus 46, 52 and/or control apparatus 54, and/or enables the acne-treatment apparatus 46, 52 and/or control apparatus 54 to output information or data to the user. For example the user interface can include a display screen for displaying one or more images of the subject, and/or the results of an analysis of one or more acne lesions on the skin of the subject. The user interface can comprise any suitable input component(s), including but not limited to a keyboard, keypad, one or more buttons, switches or dials, a mouse, a track pad, a touchscreen, a stylus, a camera, a microphone, etc., and/or the user interface can comprise any suitable output component(s), including but not limited to a display screen, one or more lights or light elements, one or more loudspeakers, a vibrating element, etc.

It will be appreciated that a practical implementation of the acne-treatment apparatus 46 and/or acne-treatment system 50 may include additional components to those shown in FIGS. 4 and 5. For example, the acne-treatment apparatus 46 and/or acne-treatment system 50 may also include a power supply, such as a battery, or components for enabling the acne-treatment apparatus 46 and/or acne-treatment system 50 to be connected to a mains power supply.

As described above, it is an objective of this disclosure to determine the inflammation phase and/or severity of an acne lesion (pimple) so that the treatment light applied to the acne lesion is adapted to the inflammation phase and/or severity to enable a more effective light treatment.

In particular it has been found that the variations in the redness (erythema), perfusion and oxygenation of blood perfusion can be used as a good discriminator to characterise the phases in the lifecycle of an acne lesion, and in particular the maturity phase of an acne lesion when the inflammation is at its peak. The blood perfusion, blood oxygenation, oxyhaemoglobin (HbO2) and haemoglobin (Hb) and the redness of the acne lesion are low in the early phase, increase in the mature phase of an acne lesion and decrease in the later phase. Therefore, one or more sensors 42 that detect parameters relating to the inflammation and/or maturity/severity phase of the acne lesions are used. For example, blood perfusion can be measured using a laser speckle contrast analysis (LASCA) device/imaging sensor, a laser Doppler monitor, a PPG sensor or an imaging PPG sensor. As another example, the HbO2 and/or Hb component can be measured using multispectral illumination and a multispectral imaging sensor. In another example, redness can be measured using a RBX-red filter from the VISIA skin analysis system. In a further example, the temperature of the acne lesion can be measured using a temperature sensor. Any combination of these or similar sensors can be used to measure parameters relating to the inflammation and/or severity of an acne lesion.

Thus, according to the techniques described herein, a light treatment is applied to an acne lesion, with the light treatment comprising applying first treatment light that is generally red light and second treatment light that is generally blue/violet light. The predominately/generally red light has wavelengths predominately in the range from 600 to 700 nm, and the generally/predominately blue/violet light has wavelengths predominately in the range from 400 to 480 nm. The ratio of the intensity of the red light to the intensity of the blue/violet light (referred to as the "light-intensity ratio") is adjusted or set based on the degree of inflammation and/or severity phase of the acne lesion determined from the measurement signal(s).

In some embodiments, based on the parameter measurements, a particular acne lesion can be classified into either (i) a relatively low degree of inflammation/relatively high severity, or (ii) a relatively high degree of inflammation/relatively low severity. If the acne lesion is determined to have a relatively low degree of inflammation/relatively high severity, then the light-intensity ratio can be in the range of 0.5 to 1.7, and if the acne lesion is determined to have a relatively high degree of inflammation/relatively low severity, then the light-intensity ratio can be above 2. The specific value of the light-intensity ratio that is used in case a relatively low degree of inflammation/relatively high severity is detected can be predefined, i.e. a predefined value in the range of 0.5 to 1.7. Alternatively the specific value of the light-intensity ratio that is used can be dependent on the degree of inflammation/degree of severity. The same applies to when there is a relatively high In more detail, the one or more sensors 42 can be used to measure one or more parameters of the skin of the subject. The parameter(s) are indicative of a degree of inflammation and/or a severity phase of an acne lesion on the skin, and can be any of the redness of the acne lesion, blood oxygenation in the acne lesion, haemoglobin and/or oxyhaemoglobin level in the acne lesion, and blood perfusion in the acne lesion. The sensor(s) 42 generate respective measurement signals representing the measured degree of inflammation and/or measured severity phase of the acne lesion.

The processing unit 40 receives the one or more measurement signals and determines the light-intensity ratio of intensity of the first treatment light to intensity of the second treatment light to be applied to the acne lesion. The ratio is determined based on the degree of inflammation and/or the severity phase of the acne lesion represented by the one or more measurement signals. The intensity of the treatment light can also be understood as an irradiance level or dose level.

Then, the processing unit 40 controls the one or more light sources 44 of the acne-treatment apparatus 46, 52 to generate the first treatment light and the second treatment light according to the determined light-intensity ratio for application to the acne lesion. Thus, the processing unit 40 can output a suitable control signal to the light source(s) 44 so that the light source(s) 44 generate the required treatment light.

In some embodiments, the processing unit 40 determines the light-intensity ratio by processing the measurement signals to determine the light-intensity ratio of the intensity of the first treatment light to the intensity of the second treatment light that is be applied to the acne lesion. The processing unit 40 determines the light-intensity ratio based on the indicated degree of inflammation and/or the indicated severity phase of the acne lesion represented by the one or more measurement signals. In some embodiments, the processing unit can determine the light-intensity ratio by comparing the determined degree of inflammation and/or the determined severity phase to one or more thresholds, or by using a look-up table that relates values of the determined degree of inflammation and/or the determined severity phase to specific values of the light-intensity ratio. For example, if the degree of inflammation is above a threshold, a first value for the light-intensity ratio can be used, and if the degree of inflammation is below the threshold, a second value for the light-intensity ratio can be used. Likewise for the severity phase.

In an alternative approach, the processing unit 40 determines the light-intensity ratio directly from the one or more measurement signals. For example the processing unit 40 can determine the light-intensity ratio by comparing the one or more measurement signals to one or more thresholds, or by using a look-up table that relates values of the one or more measurement signals or characteristics of the one or more measurement signals to specific values of the light-intensity ratio.

In some embodiments, the processing unit 40 is configured to determine the light-intensity ratio such that the light-intensity ratio increases (or is high) when the indicated degree of inflammation increases (or is high) or the indicated severity of the acne lesion decreases (or is low). Likewise, the processing unit 40 is configured to determine the light-intensity ratio such that the light-intensity ratio decreases (or is lower) when the indicated degree of inflammation decreases (or is low) or the indicated severity increases (or is high).

In particular embodiments, the processing unit 40 is configured to determine the light-intensity ratio such that the light-intensity ratio is in the range of 0.5-1.7 if the indicated degree of inflammation is in a first range of relatively low indicated inflammation values or the indicated severity is in a first range of relatively high indicated severity values, and to determine a light-intensity ratio above 2 if the indicated degree of inflammation is in a second range of relatively high indicated inflammation values or the indicated severity is in a second range of relatively low indicated severity values.

In some embodiments, the processing unit 40 controls the one or more light sources 44 to generate the first treatment light and the second treatment light simultaneously. That is, both the first treatment light and the second treatment light are generated and applied to the acne lesion at the same time. The intensity with which each of the first treatment light and the second treatment light is emitted is according to the determined light-intensity ratio.

For safety reasons (e.g. to avoid the skin from being overheated), the processing unit 40 can control the light source(s) 44 such that the total intensity or total amount of light applied to the acne lesion or skin by the light source(s) 44 is below a threshold value. That is, the processing unit 40 can not only determine a suitable light-intensity ratio to treat the acne lesion, but determine this ratio such that the total intensity of the first and second treatment lights emitted to achieve this ratio is below the threshold value.

Alternatively, rather than emit the first treatment light and the second treatment light simultaneously, the first treatment light and the second treatment light can be applied alternately. This can be useful where there is a limit to the amount of light that can be safely applied to the skin in a given time period, as it enables each of the first treatment light and second treatment light to be delivered with a higher respective intensity and improve the physiological effect of the treatment light. Thus, in alternative embodiments, the processing unit 40 controls the one or more light sources 44 to alternately generate the first treatment light and the second treatment light such that the intensities of the first treatment light and the second treatment light generated over a time period satisfy the determined ratio. Thus in these embodiments the first treatment light and the second treatment light can be alternately pulsed to treat the acne lesion. Each of the first treatment light and the second treatment light can be pulsed on and off, for example with a frequency of the order of 1 Hz-60 Hz, although those skilled in the art will appreciate that higher or lower frequencies can be used. This pulsing/alternate operation can be considered as a duty cycle. Within the duty cycle it may be that either the first treatment light or the second treatment light is being emitted, or it may be that there is also a 'no light' part of the duty cycle in addition to the first treatment light and second treatment light parts where no light is emitted by the light source(s) 44. The 'on' times for the first treatment light and the second treatment light within the duty cycle may be the same duration, or they may be different.

In embodiments where the first treatment light and second treatment light are emitted according to a duty cycle, the light-intensity ratio is dependent on the treatment light duty cycle, i.e. the proportion of time that the first treatment light is emitted to the time that the second treatment light is emitted, and the intensity with which the first treatment light and the second treatment light is emitted in their respective parts of the duty cycle. Thus, in some embodiments, the light-intensity ratio determined by the processing unit 40 can be achieved by adjusting the duty cycle. For example, to increase the light-intensity ratio, the duty cycle can be adjusted so that the first treatment light is emitted for more of the duty cycle than previously, and/or the second treatment light is emitted for less of the duty cycle than previously. In addition or alternatively, the duty cycle can be adjusted so that the first treatment light is emitted at a higher intensity than previously, and/or the second treatment light is emitted at a lower intensity than previously.

Figure 6:
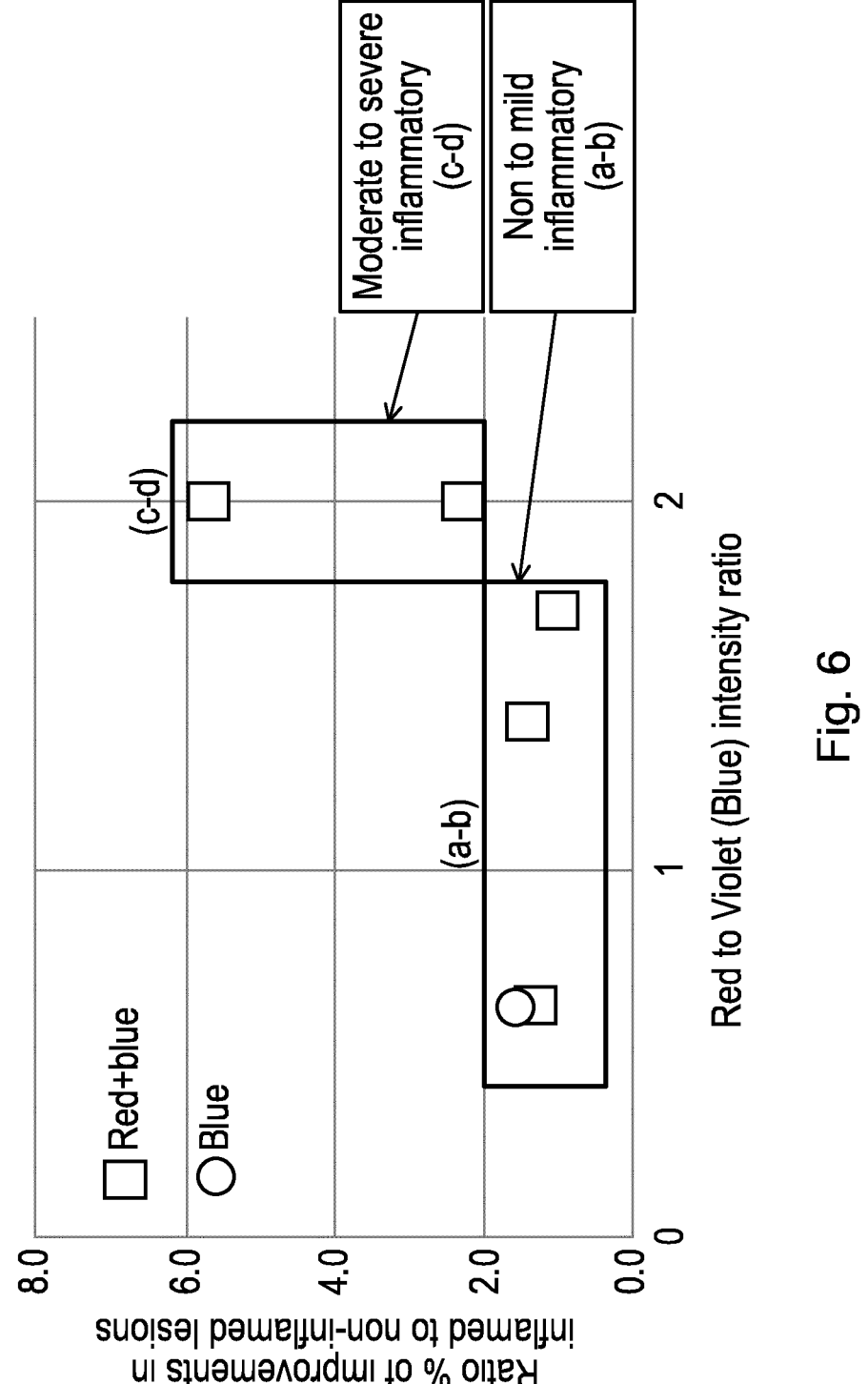
FIG. 6 is a graph illustrating a ratio of improvements of inflammatory to non-inflammatory lesions as a function of intensity ratio of red to violet/blue light.

The improvements obtained using the above techniques on high inflammation acne lesions and non- or low-inflammation acne lesions is illustrated in FIG. 6. FIG. 6 shows a ratio of improvements of inflammatory to low- or non-inflammatory acne lesions as a function of the light-intensity ratio of red to violet (indicated by the squares in FIG. 6) based on five clinical studies and compared with a study performed with blue light (indicated by the circles). The ratio of percentage of improvements in inflamed to non-inflamed acne lesions is calculated by dividing the percentage of improvements obtained in inflamed lesions by the percentage of improvements obtained in non-inflamed acne lesions. It is observed in FIG. 6 that the mean improvements in high inflammation acne lesions is higher when the ratio of red light to violet light is between 2 and 4, whereas in low- or non-inflammation acne lesions the ratio of red light to violet light is between 0.5 and 1.7. It is observed that a combined red and blue light treatment with an intensity ratio of 0.5 is better than using blue light alone for a low or non-inflammatory acne lesion.

In some embodiments, further measurements of the parameter(s) for a previously-treated acne lesion can be obtained by the sensor(s) 42 (for example several minutes or several hours after the treatment), and the further measurements analysed to monitor the effectiveness of the light treatment. In particular a comparison of the further measurements to the initial measurements (that were used to determine the light-intensity ratio used for the initial treatment) can indicate whether the inflammation or severity level of the acne lesion has decreased.

In some embodiments, particularly (but not exclusively) where the processing unit 40 is separate from the acne-treatment apparatus 52, the acne-treatment apparatus 52 can be implemented in the form of a textile or other flexible material, in which the light source(s) 44 are embedded or otherwise integrated. Such a textile or flexible material can be placed on the face or other relevant body part, and the light source(s) 44 activated to emit the required treatment light to treat acne lesions on the skin. Preferably the textile or other flexible material comprises several light sources 44 dispersed over the textile/material so that each light source 44 can be used to treat respective parts of the skin (and thus respective acne lesions). In this case, the measurements from the sensor(s) 42 can be used to determine the inflammation stage and/or severity of different acne lesions on the skin, and this information used to control the light sources 44 adjacent to different parts of the skin according to the localised inflammation/severity.

In other embodiments, the acne-treatment apparatus 52 can be implemented in the form of a pen or other small handheld device that comprises the light source(s) 44 behind a treatment window through which treatment light from the light source(s) 44 is emitted on to the skin of the subject. Such a device can be placed on or adjacent to a particular acne lesion on the skin, a measurement of the acne lesion obtained using the sensor(s) 42, and the light source(s) 44 controlled accordingly to emit the required treatment light to treat the acne lesion. The device can then be moved to another location with another acne lesion and the process repeated.

Therefore there is provided an acne-treatment system comprising a processing unit and an acne-treatment apparatus that can be used with, or as part of, a personal care device (including shaving systems) to provide an improved treatment of acne lesions. The processing unit controls light source(s) of the acne-treatment apparatus to provide appropriate red and blue light intensities based on the current physiological stage of the acne lesion, and thereby improve the treatment efficacy and reduce side effects.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An acne-treatment system comprising a processing unit and an acne-treatment apparatus having one or more light sources configured and arranged to generate first treatment light having wavelengths predominantly in a range from 600 to 700 nm and second treatment light having wavelengths predominantly in a range from 400 to 480 nm for application to an acne lesion on skin of a subject during use of the acne treatment system, the processing unit being configured to:

receive one or more measurement signals provided by one or more sensors that are configured and arranged to measure one or more parameters indicative of a degree of inflammation and/or a severity phase of the acne lesion, said one or more measurement signals representing an indicated degree of inflammation and/or an indicated severity phase of the acne lesion;

determine a light-intensity ratio of intensity of the first treatment light to intensity of the second treatment light to be applied to the acne lesion based on the indicated degree of inflammation and/or the indicated severity phase of the acne lesion represented by the one or more measurement signals; and control the one or more light sources of the acne-treatment apparatus to generate the first treatment light and the second treatment light according to the determined light-intensity ratio for application to the acne lesion.

2. An acne-treatment system as claimed in claim 1, wherein the processing unit is configured to determine the degree of inflammation and/or the severity phase of the acne lesion by processing the one or more measurement signals, and to determine the light-intensity ratio based on the determined degree of inflammation and/or the determined severity phase.

3. An acne-treatment system as claimed in claim 2, wherein the processing unit is configured to determine the light-intensity ratio by comparing the determined degree of inflammation and/or the determined severity phase to one or more thresholds, or by using a look-up table that relates values of the determined degree of inflammation and/or the determined severity phase to specific values of the light-intensity ratio.

4. An acne-treatment system as claimed in claim 1, wherein the processing unit is configured to determine the light-intensity ratio directly from the one or more measurement signals.

5. An acne-treatment system as claimed in claim 4, wherein the processing unit is configured to determine the light-intensity ratio by comparing the one or more measurement signals to one or more thresholds, or by using a look-up table that relates values of the one or more measurement signals or characteristics of the one or more measurement signals to specific values of the light-intensity ratio.

6. An acne-treatment system as claimed in claim 1, wherein the processing unit is configured to determine the light-intensity ratio such that the light-intensity ratio increases when the indicated degree of inflammation increases or the indicated severity of the acne lesion decreases, and the light-intensity ratio decreases when the indicated degree of inflammation decreases or the indicated severity increases.

7. An acne-treatment system as claimed in claim 1, wherein the processing unit is configured to determine the light-intensity ratio such that the light-intensity ratio is in a range of 0.5-1.7 if the indicated degree of inflammation is in a first range of relatively low indicated inflammation values or the indicated severity is in a first range of relatively high indicated severity values, and such that the light-intensity ratio is above 2 if the indicated degree of inflammation is in a second range of relatively high indicated inflammation values or the indicated severity is in a second range of relatively low indicated severity values.

8. An acne-treatment system as claimed in claim 1, wherein the processing unit is configured to control the one or more light sources of the acne-treatment apparatus to generate the first treatment light and the second treatment light simultaneously.

9. An acne-treatment system as claimed in claim 1, wherein the processing unit is configured to control the one or more light sources of the acne-treatment apparatus to alternately generate the first treatment light and the second treatment light such that the intensities of the first treatment light and the second treatment light generated over a time period satisfy the determined ratio.

10. An acne-treatment system as claimed in claim 1, wherein the processing unit is configured to determine the intensity of the first treatment light to be applied to the acne lesion and the intensity of the second treatment light to be applied to the acne lesion such that a total intensity of treatment light applied by the one or more light sources of the acne-treatment apparatus to the acne lesion is below a threshold value.

11. An acne-treatment system as claimed in claim 1, wherein the one or more parameters indicative of the degree of inflammation of the acne lesion comprises at least one of: redness of the acne lesion, blood oxygenation in the acne lesion, haemoglobin and/or oxyhaemoglobin level in the acne lesion, temperature of the acne lesion and blood perfusion in the acne lesion.

12. An acne-treatment system as claimed in claim 1, wherein the acne-treatment apparatus comprises the processing unit.

13. An acne-treatment system as claimed in claim 12, wherein the acne-treatment apparatus further comprises the one or more sensors configured and arranged to provide, during use of the acne-treatment apparatus, the one or more measurement signals received by the processing unit.

14. An acne-treatment system as claimed in claim 13, wherein the one or more sensors comprises one or more of an imaging sensor, a laser speckle contrast analysis, LASCA, imaging sensor, a laser Doppler perfusion monitor, a photoplethysmogram, PPG, imaging sensor, a PPG sensor, a skin reflectance sensor, a temperature sensor and a multispectral/hyperspectral imaging sensor.

15. An acne-treatment system as claimed in claim 1, wherein:

the acne-treatment system comprises a control apparatus comprising the processing unit and a first communication unit;

the acne-treatment apparatus has a second communication unit configured to communicate with the first communication unit; and during use, a control signal generated by the processing unit to control the one or more light sources of the acne-treatment apparatus is communicated from the control apparatus to the acne-treatment apparatus via the first and second communication units.

16. An acne-treatment system as claimed in claim 15, further comprising the one or more sensors configured and arranged to provide, during use of the acne-treatment system, the one or more measurement signals received by the processing unit, the one or more sensors being arranged in the control apparatus or in the acne-treatment apparatus.

17. An electric shaving apparatus comprising an acne-treatment system as claimed in claim 1, and further comprising a main body and a shaving unit coupled to the main body, wherein the one or more light sources of the acne-treatment apparatus are arranged in the shaving unit to apply the first treatment light and the second treatment light to the skin of the subject during operation of the shaving unit with the shaving unit in contact with the skin of the subject.

* * * * *